United States Patent [19]
Duncan et al.

[11] Patent Number: 5,062,799
[45] Date of Patent: Nov. 5, 1991

[54] INTERFACE MATRIX FOR DENTAL RESTORATION

[76] Inventors: Frank L. Duncan, 210-15 Northern Blvd., Bayside, N.Y. 11361; Vincent Chiaramonte, 113 Mayfield Dr., Mastic Beach, N.Y. 11951

[21] Appl. No.: 420,943

[22] Filed: Oct. 13, 1989

[51] Int. Cl.$^5$ ............................................. A61C 5/00
[52] U.S. Cl. ................. 433/215; 433/212.1; 106/35
[58] Field of Search .................. 433/203.1, 212.1, 215, 433/217.1, 222.1, 226, 228.1, 180; 264/19, 20; 106/35

[56] References Cited

U.S. PATENT DOCUMENTS

| | | | |
|---|---|---|---|
| 4,392,828 | 7/1983 | Ehrnford | 433/228.1 |
| 4,473,353 | 9/1984 | Greggs | 433/215 |
| 4,516,938 | 5/1985 | Hall | 433/215 |

Primary Examiner—Cary E. O'Connor

[57] ABSTRACT

Dental restoration. A glass filament mesh matrix has inner and outer faces, the inner face being adapted to be bonded to a natural tooth. An outer face of proper color is adapted to receive the final buildup of composite. The process of applying dental surface restoration matrix to the face of an existing natural tooth, comprising the following steps:
  a. Lubricating the surface of the natural tooth,
  b. Applying a glass filament matrix to the natural tooth, the matrix being impregnated with curable material,
  c. Curing the matrix,
  d. Removing the matrix from the natural tooth,
  e. Applying composite surface material of the proper color to the outer surface of the matrix,
  f. Replacing the matrix on the natural tooth with a bonding agent,
  g. Curing the matrix by either heat or light.

3 Claims, 1 Drawing Sheet

INTERFACE MATRIX FOR DENTAL RESTORATION

TECHNICAL FIELD

This invention relates to dental restoration and more particularly, to cosmetic bonding.

The object of the invention is to allow either the Dentist or Laboratory Technician to fabricate a more precise addition to a natural tooth by:
1. having a better control of color (shade match).
2. easier chairside or laboratory buildup and adjustment.
3. ability to impart a three dimensional effect in the final restoration.
4. less Dentist and Laboratory time spent in construction.

PRIOR ART AND BACKGROUND

The present state of the art consists of two processes:
1. Chairside bonding process, where the Dentist builds the desired shape, color and size of an addition to a natural tooth using a composite material. He does this by laminating layers of composite over the surface of a prepared, etched natural tooth. The chairside method is both difficult and time consuming and only when completed does the Dentist or Patient realize the aesthetic value of the work done. This addition to the natural tooth is permanently bonded from the very beginning of the operation and cannot be removed for any simple addition or adjustment.
2. The Laboratory process, which is constructed as a finished product completed on casts of a natural tooth using either resins or porcelain.

In this invention, the Laboratory processed veneer has greater density and strength and allows for the Dentist and Patient to evaluate the aesthetic value before bonding permanently.

PROBLEMS

A. Poor coloring of the natural tooth: The only way this problem can be corrected by either the Lab process or Dentist buildup is by increasing the thickness of the buildup. This will result in an oversized, bulky restoration. The only alternative would be for the Dentist to remove some natural tooth structure allowing for more thickness, a more aesthetic final product.

The Invention:

This invention consists of a thin shell called the matrix, which is opacified to completely mask the underlying color of the natural tooth. This shell matrix is approximately three tenths of a millimeter in thickness and is adapted uniformly to the surface of the natural tooth. The result is a uniform, natural looking finished product.

B. Poor bonding at the interface of the natural tooth:

The composites on the market are: Filled, lightly filled and unfilled. If one uses a highly filled or lightly filled composite, the fill in the composite will actually act as a repellent to a complete bond at the interface of the natural tooth. If one trIes to compensate by using combinations of materials they would be applied in an uneven manner further creating problems.

This invention, consisting of a thin shell, has two receiving surfaces, the buildup interface and the tooth interface. (FIGS. 1 and 2) Due to its design, each of the interfaces are coated with the proper materials to accept either the cementing medium or the buildup medium.

The lightly filled resins are best for bonding purposes while the heavy filled resins are best for the outer surface because of its abrasion resistance.

C. Predicatable thickness of the final product: Using the state of the art technique, this cannot be achieved until the finish of the restoration and only the eye can decide this finished state.

This invention easily compensates for this problem because the matrix is three tenths of a m.m. (0.3 mm) thick and adding two tenths of a m.m. of shading material over this results in a restoration exactly five tenths of a m.m. ( 0.5 mm) of thickness in the final product.

D. Strength: The strength of the materials on the market are only what the strength of the composite materials possess. This invention utilizes an interlocked weave of glass filaments in the matrix, which adds to the overall strength of the completed restoration.

OBJECTS OF THE INVENTION

The principal object of the invention is to provide new and improved dental restoration means and methods.

Another object of the invention is to provide new and improved cosmetic bonding for dental restoration.

Another object of the invention is to provide new and improved cosmetic bonding for dental restorations using interlocking glass filaments.

Another object of the invention is to provide new and improved dental restoration means comprising: an interlocking glass filament matrix, having inner and outer faces, the inner face being adapted for bonding to the natural tooth and an outer face with proper depth of color adapted for receiving the final buildup of the veneer.

These and other objects of the invention will be apparent from the following specification and drawings.

BEST MODE OF THE INVENTION

Figure 1:
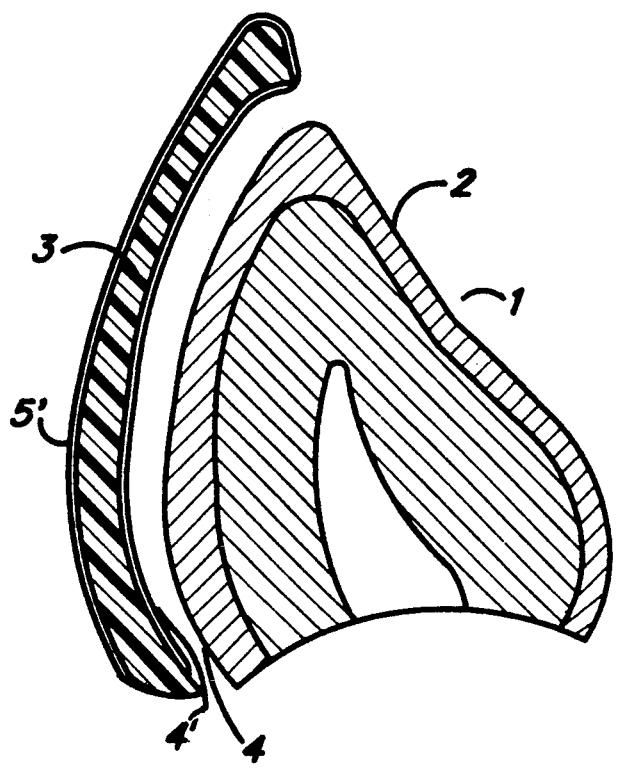
FIGS. 1 and 2 show sectional views of an embodiment of the invention.

FIG. 1 shows a sectional view of a natural tooth 1, having an outer enamel surface 2. An interlocking glass filament mesh 3 is placed over the outer surface 4, of the tooth. A composite surface layer 5, is placed on the outer surface of the glass filament mesh 3. The glass filament mesh, is bonded to the tooth surface with compatible bonding material 4' and the outer surface of the glass filament mesh is bonded by bonding material 5' to the surface material 5, FIG. 2, which is chosen to have the proper color.

Figure 2:
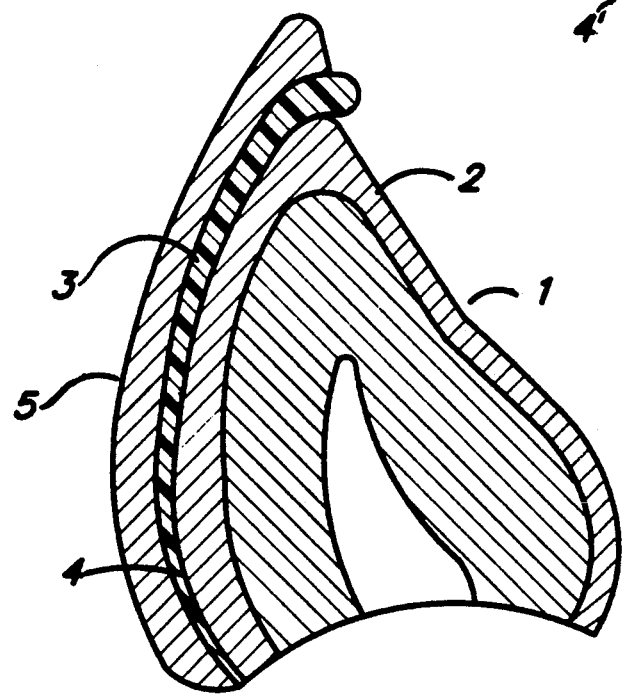

FIG. 2 shows the complete assembly.

In the manufacture of the "matrix", the filament glass mesh acts as a mixing device, allowing the tooth surface bonding material to mix with the buildup surface bonding material prior to its curing. After curing, the resulting shell, or matrix, becomes rigid and is 3/10 of a m.m. (0.3 mm) in thickness. If both the outer surface material and the inner surface material are dissimilar, they will chemically combine in the uncured state thus allowing different materials on the market a new outlet. Example: where methyl methacrolate bonds poorly to a Bis G.M.A. material when either is in the cured state, the interface matrix itself may be treated in its manufacture to receive a methyl methacrolate surface on either side.

Compositions that are state of the art today are Bis G.M.A. resins. With our interface, we can actually add a dissimilar material such as acrylic (methyl methacrolate) to either the tooth surface or the buildup surface (outer surface).

Then after curing, they are chemically combined. If each surface was cured separately, and then cured together, they would not chemically combine. Therefore, the final matrix would have two surfaces for different purposes.

When the cured matrix is lined up to the tooth, but not bonded to the tooth, either the Dentist or Lab Technician can now build up a composite material on the buildup surface of the matrix, restoring the desired anatomy and color. If the Dentist, building up chairside, decides to remove the veneer from the tooth for better application in hand, he may do so due to the fact that the tooth surface of the matrix is not yet bonded to the tooth. When he has completed the desired anatomy, and has decided no further work has to be done, he can permanently bond the veneer to the natural tooth by using an autocure or light cure cementing material compatible with the tooth surface interface of the matrix. The Laboratory procedure is similar, except, working is done on casts.

Laboratory Process:

1. The matrix supplied either to the Laboratory or Dentist comprises a glass filament pad, saturated on both sides with the proper material in a pliable, uncured consistency, sealed from exposure to light in a capsule or between plastic coated sheets of paper. This pad, which is pre-shaped to the approximate size of the natural tooth, is adapted to the tooth surface which has been lubricated to prevent bonding at this stage, and then cured by light application or heat cured depending on selection.

After curing, the pad now being rigid, can accept the proper buildup of composite on the bonding surface of the matrix. Due to the lubricated tooth surface, the entire system may be removed from the tooth where further work may be done more conveniently. Upon completion of the desired anatomy, the facing is ready to be bonded to the natural tooth. This is done by cleaning the surface of the tooth with a de-greasing medium, then etching the tooth enamely properly The tooth surface interface of the veneer is also de-greased and lightly scored. The proper cementing medium is applied and the facing is auto-cured in place.

2. Laboratory Kit: This kit consists of all separate components that will allow the Laboratory to fabricate the matrix on casts, saving the Dentist valuable chair time. The Laboratory may also complete the buildup for the final veneer, sending the Dentist the completed restoration. The Laboratory may also be supplied with a factory cured matrix that has an approximate size and shape. The Lab then relines this matrix to the cast thereby forming a precise fit.

It is claimed:

1. The process of applying a dental surface restoration matrix to the face of an existing natural tooth, comprising the following steps; a. lubricating the surface of the natural tooth, b. forming a glass filament matrix having inner and outer surfaces on the natural tooth, coating the matrix with a first curable material on the outer face and a second curable material on the inner face, c. curing the matrix assembly, d. removing the matrix assembly from the natural tooth, e. applying composite surface material of the proper color to the first material on the outer surface of the matrix, f. replacing the matrix assembly on the natural tooth with a bonding agent.

2. Laboratory process of making a dental surface restoration comprising the following steps: a. making a casting of the natural tooth, b. forming a glass filament matrix on the outer surface of the tooth casting, coating the matrix with a first curable hardening material on one side and a second curable material on the other side, c. curing the matrix using either light of heat, d. removing the matrix from the casting, e. applying to the matrix an outer surface of composite material of proper color to form an assembly, f. returning the completed assembly to the Dentist for application to the patient.

3. Dental restoration means comprising: a glass filament matrix, an inner face and an outer face of different materials attached to the matrix, the inner face being adapted to bond to a natural tooth and the outer face being adapted to be bonded to a layer of composite material simulating a natural tooth.

* * * * *